United States Patent [19]
Elbe et al.

[11] Patent Number: 6,107,336
[45] Date of Patent: Aug. 22, 2000

[54] DIHYDROFURAN CARBOXAMIDES

[75] Inventors: Hans-Ludwig Elbe, Wuppertal; Franz Kunisch, Odenthal; Dietmar Bielefeldt, Ratingen; Ralf Tiemann, Leverkusen; Klaus Stenzel, Düsseldorf; Stefan Dutzmann, Langenfeld; Martin Kugler, Leichlingen; Heinrich Schrage, Krefeld, all of Germany

[73] Assignee: Bayer Aktiengesellschaft, Leverkusen, Germany

[21] Appl. No.: 09/230,198

[22] PCT Filed: Jul. 11, 1997

[86] PCT No.: PCT/EP97/03693

§ 371 Date: Jan. 20, 1999

§ 102(e) Date: Jan. 20, 1999

[87] PCT Pub. No.: WO98/03495

PCT Pub. Date: Jan. 29, 1998

[30]     Foreign Application Priority Data

Jul. 24, 1996 [DE] Germany .......................... 196 29 825

[51] Int. Cl.$^7$ .......................... A01N 43/08; C07D 307/30
[52] U.S. Cl. ............................ 514/471; 549/487
[58] Field of Search .................. 549/487; 514/471

[56]            References Cited

U.S. PATENT DOCUMENTS

| 5,223,526 | 6/1993 | McLoughlin et al. | 514/406 |
| 5,330,995 | 7/1994 | Eicken et al. | 514/355 |
| 5,438,070 | 8/1995 | Eicken et al. | 514/403 |
| 5,480,897 | 1/1996 | Eicken et al. | 514/365 |
| 5,556,988 | 9/1996 | Eicken et al. | 548/374.1 |
| 5,589,493 | 12/1996 | Eicken et al. | 514/355 |

FOREIGN PATENT DOCUMENTS 44 45 545  6/1996  Germany .
1215066   12/1970  United Kingdom .

OTHER PUBLICATIONS

Patent Abstracts of Japan, vol. 014, No. 417, 1990 & JP 02–157266 Mitsubishi Kasei Corp.
Journal of Pesticide Science, vol. 18, No. 3, Aug. 1993, pp. 245–251.
Chemische Berichte, 104 (month unavailable), 1971, pp. 734–738.

*Primary Examiner*—Bernard Dentz
*Attorney, Agent, or Firm*—Joseph C. Gil; Carol Marmo

[57]            ABSTRACT

The invention concerns novel dihydrofuran carboxamides of formula (I),

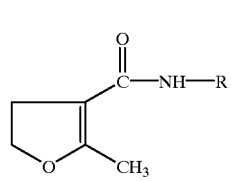

in which R stands for groups of formulae (a), (b) or (c),

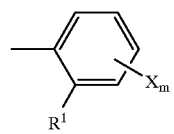

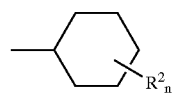

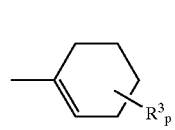

in which $R^1$, $R^2$, $R^3$, X, m, n and p have the meanings given in the description. The invention also concerns a process for preparing the novel substances, and their use for combating undesirable micro-organisms for plant- and material-protection purposes.

5 Claims, No Drawings

DIHYDROFURAN CARBOXAMIDES

This application is a 371 of PCT/EP97/03693 filed Jul. 7, 1997.

TECHNICAL FIELD OF THE INVENTION

The present invention relates to novel dihydrofurancarboxamides, to a process for their preparation and to their use as microbicides.

BACKGROUND OF THE INVENTION

It is already known that certain dihydrofurancarboxanilides have fungicidal properties (cf. DE-A 1 914 954 and J. Pesticide Sci. 18 (1993), 245–251). Thus, for example, 2-methyl-4,5-dihydrofuran-3-carboxanilide and 2-methyl-4,5-dihydrofuran-3-N-(1,1,3-trimethyl-indan-4-yl)-carboxamide can be used for controlling fungi. The activity of these compounds is good, but in some cases leaves something to be desired at low application rates.

DETAILED DESCRIPTION OF THE INVENTION

This invention, accordingly, provides novel dihydrofuran-carboxamides of the formula

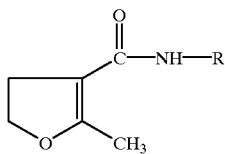

(I)

in which

R represents groupings of the formulae

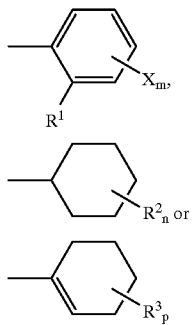

in which

R$^1$ represents optionally substituted cycloalkyl, optionally substituted bicycloalkyl, optionally substituted cycloalkenyl, optionally substituted cycloalkylalkyl, optionally substituted aryl, optionally substituted aroxy, optionally substituted aralkyl or represents alkyl, X represents alkyl having 1 to 6 carbon atoms, halogen, cycloalkyl having 3 to 8 carbon atoms, alkoxy having 1 to 6 carbon atoms, halogenoalkyl having 1 to 4 carbon atoms and 1 to 5 halogen atoms or halogenoalkoxy having 1 to 4 carbon atoms and 1 to 5 halogen atoms, m represents integers from 0 to 3, R$^2$ represents alkyl, cycloalkyl, optionally substituted aryl or optionally substituted aralkyl, n represents integers from 0 to 3, R$^3$ represents alkyl, cycloalkyl, optionally substituted aryl or optionally substituted aralkyl and p represents integers from 0 to 3.

Furthermore, it has been found that dihydrofuran-carboxamides of the formula (I) are obtained when 2-methyl-4,5-dihydrofuran-3-carbonyl halides of the formula

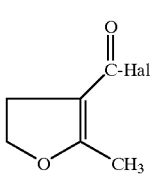

(II)

in which

Hal represents chlorine or bromine, are reacted with amines of the formula $$H_2N—R \qquad (III)$$

in which

R is as defined above, if appropriate in the presence of an acid binder and if appropriate in the presence of a diluent.

Finally, it has been found that the novel dihydrofuran-carboxamides of the formula (I) have very good microbicidal properties and can be employed for controlling undesirable microorganisms both in crop protection and in the protection of materials.

Surprisingly, the dihydrofuran-carboxamides according to the invention have considerably better fungicidal activity than 2-methyl-4,5-dihydrofuran-3-carboxanilide and 2-methyl-4,5-dihydrofuran-3-N-(1,1,3-trimethylindan-4-yl)-carboxamide, which are constitutionally similar prior-art active compounds of the same direction of action.

The formula (I) provides a general definition of the dihydrofuran-carboxamides according to the invention.

R preferably represents the groupings of the formulae

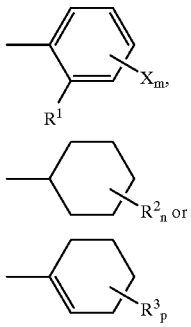

in which

R$^1$ preferably represents cycloalkyl having 3 to 8 carbon atoms which is optionally mono- to trisubstituted by identical or different alkyl groups having 1 to 4 carbon atoms, represents bicycloalkyl having 7 to 12 carbon atoms which is optionally mono- to trisubstituted by identical or different alkyl groups having 1 to 4 carbon atoms, represents cycloalkenyl having 5 to 8 carbon atoms which is optionally mono- to trisubstituted by identical or different alkyl groups having 1 to 4 carbon atoms or represents cycloalkylalkyl having 3 to 8 carbon atoms in the cycloalkyl moiety and 1 to 4 carbon atoms in the alkyl moiety which is optionally mono- to trisubstituted by identical or different alkyl groups having 1 to 4 carbon atoms, or represents phenyl which may be mono- to trisubstituted by identical or different substituents selected from the group consisting of halogen and alkyl having 1 to 4 carbon atoms, or represents phenoxy which may be mono- to trisubstituted by identical or different substituents selected from the group consisting of halogen and alkyl having 1 to 4 carbon atoms, or represents phenylalkyl having 1 to 4 carbon atoms in the alkyl moiety which may be mono- to trisubstituted in the phenyl moiety by identical or different substituents selected from the group consisting of halogen and alkyl having 1 to 4 carbon atoms, or represents straight-chain or branched alkyl having 1 to 12 carbon atoms, X preferably represents straight-chain or branched alkyl having 1 to 4 carbon atoms, fluorine, chlorine, bromine, cycloalkyl having 3 to 8 carbon atoms, straight-chain or branched alkoxy having 1 to 4 carbon atoms, halogenoalkyl having 1 or 2 carbon atoms and 1 to 5 fluorine, chlorine and/or bromine atoms or represents halogenoalkoxy having 1 or 2 carbon atoms and 1 to 5 fluorine, chlorine and/or bromine atoms, m preferably represents the numbers 0, 1 or 2, $R^2$ preferably represents straight-chain or branched alkyl having 1 to 12 carbon atoms, cycloalkyl having 3 to 8 carbon atoms, phenyl which is optionally mono- to trisubstituted by identical or different substituents selected from the group consisting of halogen and alkyl having 1 to 4 carbon atoms or represents phenylalkyl having 1 to 4 carbon atoms in the alkyl moiety which is optionally mono- to trisubstituted by identical or different substituents selected from the group consisting of halogen and alkyl having 1 to 4 carbon atoms, n preferably represents the numbers 0, 1, 2 or 3, $R^3$ preferably represents straight-chain or branched alkyl having 1 to 12 carbon atoms, cycloalkyl having 3 to 8 carbon atoms, phenyl which is optionally mono- to trisubstituted by identical or different substituents selected from the group consisting of halogen and alkyl having 1 to 4 carbon atoms or represents phenylalkyl having 1 to 4 carbon atoms in the alkyl moiety which is optionally mono- to trisubstituted by identical or different substituents selected from the group consisting of halogen and alkyl having 1 to 4 carbon atoms and p preferably represents the numbers 0, 1, 2 or 3.

Particular preference is given to dihydrofurancarboxamides of the formula (I) in which R represents a grouping of the formula

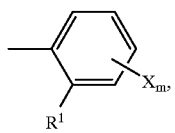

-continued

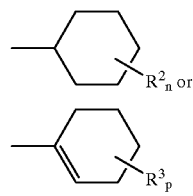

in which $R^1$ represents cycloalkyl having 3 to 8 carbon atoms which is optionally mono- to trisubstituted by identical or different substituents selected from the group consisting of methyl, ethyl, n-propyl, isopropyl and tert-butyl, or represents bicycloalkyl having 7 to 12 carbon atoms which is optionally mono- to trisubstituted by identical or different substituents selected from the group consisting of methyl, ethyl, n-propyl, isopropyl and tert-butyl, or represents cycloalkenyl having 5 to 8 carbon atoms which is optionally mono- to trisubstituted by identical or different substituents selected from the group consisting of methyl, ethyl, n-propyl, isopropyl and tert-butyl, or represents cycloalkylalkyl having 3 to 8 carbon atoms in the cycloalkyl moiety and 1 or 2 carbon atoms in the alkyl moiety which is optionally mono- to trisubstituted by identical or different substituents selected from the group consisting of methyl, ethyl, n-propyl, isopropyl and tert-butyl, or represents phenyl which may be mono- to trisubstituted by identical or different substituents selected from the group consisting of fluorine, chlorine, bromine, methyl, ethyl, n-propyl, isopropyl and tert-butyl, or represents phenoxy which may be mono- to trisubstituted by identical or different substituents selected from the group consisting of fluorine, chlorine, bromine, methyl, ethyl, n-propyl, isopropyl and tert-butyl, or represents phenylalkyl having 1 or 2 carbon atoms in the alkyl moiety which may be mono- to trisubstituted in the phenyl moiety by identical or different substituents selected from the group consisting of fluorine, chlorine, bromine, methyl, ethyl, n-propyl, isopropyl and tert-butyl, or represents straight-chain or branched alkyl having 1 to 12 carbon atoms, X represents methyl, ethyl, n-propyl, isopropyl, tert-butyl, fluorine, chlorine, bromine, cyclopropyl, cyclopentyl, cyclohexyl, cycloheptyl, cyclooctyl, methoxy, ethoxy, trichloromethyl, trifluoromethyl, difluoromethyl, difluorochloromethyl, trifluoromethoxy or difluoromethoxy, m represents the numbers 0, 1 or 2, where X represents identical or different radicals if m represents 2, $R^2$ represents methyl, ethyl, n-propyl, isopropyl, n-butyl, sec-butyl, iso-butyl, tert-butyl, 2-ethylbutyl, octyl, decyl, dodecyl, cyclopropyl, cyclopentyl, cyclohexyl, cycloheptyl, cyclooctyl, phenyl which is optionally mono- or disubstituted by fluorine, chlorine, bromine, methyl, ethyl, n-propyl, isopropyl and/or tert-butyl or represents phenylalkyl having 1 or 2 carbon atoms in the alkyl moiety, where the phenyl moiety may be mono- or disubstituted by fluorine, chlorine, bromine, methyl, ethyl, n-propyl, isopropyl and/or tert-butyl, n represents the numbers 0, 1, 2 or 3, where $R^2$ represents identical or different radicals if n represents 2 or 3, $R^3$ represents methyl, ethyl, n-propyl, isopropyl, n-butyl, sec-butyl, iso-butyl, tert-butyl, 2-ethyl-butyl, octyl, decyl, dodecyl, cyclopropyl, cyclopentyl, cyclohexyl, cycloheptyl, cyclooctyl, phenyl which is optionally mono- or disubstituted by fluorine, chlorine, bromine, methyl, ethyl, n-propyl, isopropyl and/or tert-butyl or represents phenylalkyl having 1 or 2 carbon atoms in the alkyl moiety, where the phenyl moiety may be mono- or disubstituted by fluorine, chlorine, bromine, methyl, ethyl, n-propyl, isopropyl and/or tert-butyl and p represents the numbers 0, 1, 2 or 3, where $R^3$ represents identical or different radicals if p represents 2 or 3.

Using 2-methyl-4,5-dihydrofuran-3-carbonyl chloride and 4-fluoro-2-cyclooctyl-aniline as starting materials, the course of the process according to the invention can be illustrated by the equation below.

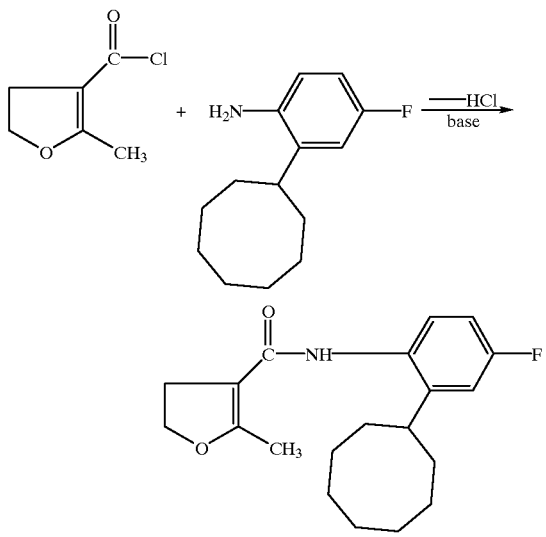

The formula (II) provides a general definition of the 2-methyl-4,5-dihydrofuran-3-carbonyl halides required as starting materials for carrying out the process according to the invention. Hal also preferably represents chlorine or bromine.

The 2-methyl-4,5-dihydrofuran-3-carbonyl halides are known or can be prepared by known methods (cf. DE-A 1 914 954 and Chem. Ber. 104 (1971), 734–738).

The formula (III) provides a general definition of the amines required as reaction components for carrying out the process according to the invention. In this formula, R preferably has those meanings which have already been mentioned as being preferred for this radical in connection with the description of the compounds of the formula (I) according to the invention.

The amines of the formula (III) are known or can be prepared by known processes (cf. U.S. Pat. No. 5,223,526, EP-A 0 545 099, EP-A 0 589 301 and DE-A 44 45 545).

Suitable acid binders for carrying out the process according to the invention are all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates such as sodium acetate, potassium acetate, calcium acetate, and also tertiary amines, such as trimethylamine, triethylamine, tributylamine, N,N-dimethylaniline pyridine, N-methylpiperidine, N,N-dimethylaminopyridine, diazabicyclooctane (DABCO), diazabicyclononene (DBN) or diazabicycloundecene (DBU). However, it is also possible to carry out the reaction without an additional acid binder, or to employ an excess of amine component, so that it simultaneously acts as acid binder.

Suitable diluents for carrying out the process according to the invention are all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl-t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide or sulphones, such as sulpholane.

When carrying out the process according to the invention, the reaction temperatures can be varied within a relatively wide range. In general, the reaction is carried out at temperatures between 0° C. and 100° C., preferably between 10° C. and 80° C.

The process according to the invention is generally carried out under atmospheric pressure. However, it is also possible to operate under elevated or reduced pressure.

When carrying out the process according to the invention, generally 1 mol or else an excess of amine of the formula (III) and 1 to 3 mol of acid binder are employed per mole of 2-methyl-4,5-dihydrofuran-3-carbonyl halide of the formula (II). However, it is also possible to employ the reaction components in other ratios. Work-up is carried out by customary methods. In general, the reaction mixture is mixed with water and the organic phase is separated off and, after drying, concentrated under reduced pressure. The residue that remains can, if required, be freed of any impurities that may still be present using customary methods, such as chromatography or recrystallization.

The compounds according to the invention have a potent microbicidal activity and can be employed for controlling undesirable microorganisms, such as fungi and bacteria, in crop protection and in the protection of materials.

Fungicides can be employed [lacuna] crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris pv. oryzae;*

Pseudomonas species, such as, for example, *Pseudomonas syringae pv. lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Altemaria species, such as, for example, *Altemaria brassicae;*

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Venturia, Podosphaera, Phytophtora and Plasmopara species. They are also very successfully used for controlling rice diseases, such as, for example, Pyricularia species.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, papers and boards, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis,*

Aspergillus, such as *Aspergillus niger,*

Chaetomium, such as *Chaetomium globosum,*

Coniophora, such as *Coniophora puetana,*

Lentinus, such as *Lentinus tigrinus,*

Penicillium, such as *Penicillium glaucum,*

Polyporus, such as *Polyporus versicolor,*

Aureobasidium, such as *Aureobasidium pullulans,*

Sclerophoma, such as *Sclerophoma pityophila,*

Trichoderma, such as *Trichoderma viride,*

Escherichia, such as *Escherichia coli,*

Pseudomonas, such as *Pseudomonas aeruginosa,*

Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure and/or solid carriers, optionally with the use of surfactants, that is emulsifiers and/or dispersants and/or foam formers. In the case of the use of water as an extender, organic solvents can, for example, also be used as auxiliary solvents. The following are mainly suitable as liquid solvents: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol and their ethers and esters, ketones, such as acetone, methyl ethyl ketone, methyl isobutyl ketone or cyclohexanone, strongly polar solvents, such as dimethylformamide or dimethyl sulphoxide, or else water. Liquefied gaseous extenders or carriers are to be understood as meaning those liquids which are gaseous at standard temperature and under atmospheric pressure, for example aerosol propellants, such as halogenated hydrocarbons, or else butane, propane, nitrogen and carbon dioxide. Suitable solid carriers are: for example ground natural minerals, such as kaolins, clays, talc, chalk, quartz, attapulgite, montmorillonite or diatomaceous earth and ground synthetic minerals, such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids, such as cephalins and lecithins, and synthetic phospholipids can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:
Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole,
dimethirimol, dimethomorph, diniconazole, diniconazole-M, dinocap, diphenylamine, dipyrithione, ditalimfos, dithianon, dodemorph, dodine, drazoxolon,
ediphenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimnidol, flusilazole, flusulfamide, flutolanil, flutriafol, folpet, fosetyl-alumninium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, imninoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G, OK-8705, OK-8801, 2',6'-dibromo-2-methyl-4'-trifluoromethoxy-4'-trifluoro-methyl-1,3-thiazole-5-carboxanilide, 2,6-dichloro-N-(4-trifluorormethylbenzyl)-benzamide, 2-aminobutane, 2-phenylphenol (OPP), 8-hydroxyquinoline sulphate, cis-1-(4-chlorophenyl)-2-(1H-1,2,4-triazol-1-yl)-cycloheptanol, (5RS,6RS)-6-hydroxy-2,2,7,7-tetramethyl-5-(1H-1,2,4-triazol-1-yl)-3-octanone, α-(2,4-dichlorophenyl)-β-methoxy-α-methyl-1H-1,2,4-triazole-1-ethanol, α-(1,1-dimethylethyl)-β-(2-phenoxyethyl)-1H-1,2,4-triazole-1-ethanol, 1-[1-[2-[(2,4-dichlorophenyl)-methoxy]-phenyl]-ethenyl]-1H-imidazole, bis-(-methylethyl)-3-methyl-4-[(3-methylbenzoyl)-oxy]-2, 5-thiophenedicarboxylate, 2,6-dichloro-N-[[4-(trifluoromethyl)-phenyl]-methyl]-benzamide, (E)-α-(methoxyimino)-N-methyl-2-phenoxy-phenylacetamide, 9H-xanthene-2-[(phenylamino)-carbonyl]-9-carboxylic hydrazide, O-methyl S-phenyl phenylpropylphosphoramidothioate, N-(5-chloro-2-methylphenyl)-2-methoxy-N-(2-oxo-3-oxazolidinyl)-acetamide, 1-(2,4-dichlorophenyl)-2-(1H-1,2,4-triazol-1-yl)

ethanone-O-(phenylmethyl)-oxime, N-(2,6-dimethylphenyl)-2-methoxy-N-(tetrahydro-2-oxo-3-thienyl)-acetamide, cis-4-[3-[4-(1,1-dimethylpropyl)-phenyl-2-methylpropyl]-2,6-dimethyl-morpholinehydrochloride, 1-(3,5-dichlorophenyl)-3-(2-propenyl)-2,5-pyrrolidindione, 1-methyl-5-nonyl-2-(phenylmethyl)-3-pyrrolidinole, 1-[[2-(4-chlorophenyl)-3-phenyloxiranyl]-methyl]-1H-1,2,4-triazole, methanetetrathiol sodium salt, 2-(2,3,3-triiodo-2-propenyl)-2H-tetrazole, N-[3-chloro-4,5-bis(2-propinyloxy)-phenyl]-N'-methoxy-methanimidamide, α-(5-methyl-1,3-dioxan-5-yl)-β-[[4-(trifluoromethyl)-phenyl]-methylene]-1H-1,2,4-triazole-1-ethanol, 1-(2-methyl-1-naphthalenyl)-1H-pyrrol-2,5-dione, N-(2,6-dimethylphenyl)-2-methoxy-N-(tetrahydro-2-oxo-3-furanyl)-acetamide, 3,4-dichloro-1-[4-(difluoromethoxy)-phenyl]-1H-pyrrol-2,5-dione, N-[2,2,2-trichloro-1-[(chloroacetyl)-amino]-ethyl]-benzamide, N-formyl-N-hydroxy-DL-alanine sodium salt, N-(4-cyclohexylphenyl)-1,4,5,6-tetrahydro-2-pyrimidinamine, 4-methyl-tetrazolo[1,5-a]quinazolin-5(4H)-one, 2-chloro-N-(2,6-dimethylphenyl)-N-(isothiocyanatomethyl)-acetamide, ethyl[(4-chlorophenyl)-azo]-cyanoacetate, N-(4-hexylphenyl)-1,4,5,6-tetrahydro-2-pyrimidinamine, N-(2-chloro-4-nitrophenyl)-4-methyl-3-nitro-benzenesulphonamide, methyl N-(chloroacetyl)-N-(2,6-dimethylphenyl)-DL-alaninate, 3-[2-(4-chlorophenyl)-5-ethoxy-3-isoxazolidinyl]-pyridine, 2-[(1-methylethyl)sulphonyl]-5-(trichloromethyl)-1,3,4-thiadiazole, spiro[2H]-1-benzopyrane-2,1'(3'H)-isobenzofuran]-3'-one, methyl N-(2,6-dimethylphenyl)-N-(5-isoxazolylcarbonyl)-DL-alaninate, potassium hydrogen carbonate, 1-[[2-(2,4-dichlorophenyl)-1,3-dioxolan-2-yl]-methyl]-1H-imidazole, 1-[(diiodomethyl)-sulphonyl]-4-methyl-benzene, 2-bromo-2-(bromomethyl)-pentanedinitrile, 2-[[6-deoxy-4-O-(4-O-methyl-β-D-glycopyranosyl)-α-D-glucopyranosyl]-amino]-4-methoxy-1H-pyrrolo[2,3-d]pyrimnidine-5-carbonitrile, methyl 1-(2,3-dihydro-2,2-dimethyl-1H-inden-1-yl)-1H-imidazole-5-carboxylate, 2-chloro-N-(2,3-dihydro-1,1,3-trimethyl-1H-inden-4-yl)-3-pyridinecarboxamide, O,O-diethyl[2-(dipropylamino)-2-oxoethyl]-ethylphosphoramidothioate, α-(2,4-dichlorophenyl)-β-fluoro-β-propyl-1H-1,2,4-triazole-1-ethanol, 3-(1,1-dimethylpropyl-1-oxo-1H-indene-2-carbonitrile, 2,6-dichloro-5-(methylthio)-4-pyrimidinyl-thiocyanate, S-methyl 1,2,3-benzothiadiazole-7-carbothioate, N-(6-methoxy)-3-pyridinyl)-cyclopropanecarboxamide, 3,5-dichloro-N-[cyano-[(1-methyl-2-propynyl)-oxy]-methyl]-benzamide, 4-chloro-2-cyano-N,N-dimethyl-5-(4-methylphenyl)-1H-imidazole-1-sulfonamide, 8-(1,1-dimethylethyl)-N-ethyl-N-propyl-1,4-dioxaspiro[4.5]decane-2-methanamine, 2,2-dichloro-N-[1-(4-chlorophenyl)ethyl]-1-ethyl-3-methyl-cyclopropanecarboxamide, N-(2,3-dichloro-4-hydroxyphenyl)-1-methyl-cyclohexanecarboxamide.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, betacyluthrin, bifenthrin, BPMC, brofenprox, bromophos A, bufencarb, buprofezin, butocarboxim, butylpyridaben,
cadusafos, carbaryl, carbofuran, carbophenothion, carbosulfan, cartap, CGA 157 419, CGA 184699 chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992 salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the preparation of active compound, or the active compound itself, into the soil. The seed of the plants can also be treated.

In the treatment of parts of plants, the active compound concentrations in the use forms can be varied within a substantial range: They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

The compositions used for the protection of industrial materials generally comprise an amount of from 1 to 95%, preferably from 10 to 75%, of the active compounds.

The use concentrations of the active compounds according to the invention depend on the species and the occurrence of the microorganisms to be controlled and on the composition of the material to be protected. The optimal rate of application can be determined by test series. In general, the use concentrations are in the range from 0.001 to 5% by weight, preferably from 0.05 to 1.0% by weight, based on the material to be protected.

It is possible to increase the activity and the activity spectrum of the active compounds which are to be used according to the invention in the protection of materials, or of the compositions, concentrates or quite generally formulations which can be prepared from these, by adding, if appropriate, other compounds having antimicrobial action, fungicides, bactericides, herbicides, insecticides or other active compounds for increasing the activity spectrum or for obtaining special effects such as, for example, additional protection against insects. These mixtures may have a wider activity spectrum than the compounds according to the invention.

The preparation and the use of the compounds according to the invention are illustrated by the examples below.

PREPARATION EXAMPLES

Example 1

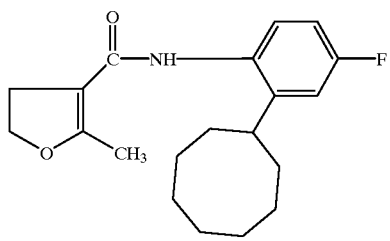

At room temperature, a solution of 1.5 g (0.01 mol) of 2-methyl-4,5-dihydrofuran-3-carbonyl chloride in 10 ml of toluene is added dropwise with stirring to a mixture of 2.2 g (0.01 mol) of 4-fluoro-2-cyclooctylaniline, 1.0 g of triethylamine and 40 ml of toluene. After the addition has ended, the reaction mixture is stirred at room temperature for another 2 hours. The reaction mixture is subsequently admixed with water. The organic phase is separated off, dried over sodium sulphate and then concentrated under reduced pressure. The residue that remains is stirred with hexane. The resulting crystalline product is filtered off with suction and dried at 50° C. under reduced pressure. In this manner, 2.2 g (66.7% of theory) of N-(4-fluoro-2-cyclooctyl)-2-methyl-4,5-dihydrofuran-3-carboxanilide are obtained in the form of a solid substance of melting point 91° C.

The dihydrofuran-carboxamides of the formula (I) listed in the Table below are prepared in a similar manner.

TABLE 1

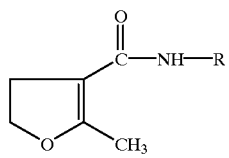
(I)

| Example No. | R | Physical constant |
|---|---|---|
| 2 | 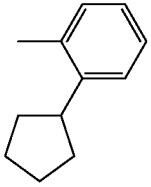 | m.p.: 91° C. |
| 3 | 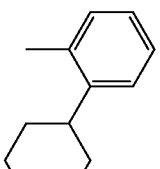 | m.p.: 104° C. |
| 4 | 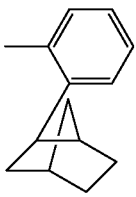 | m.p.: 123° C. |
| 5 | 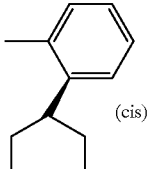 (cis) | m.p.: 65° C. |
| 6 | 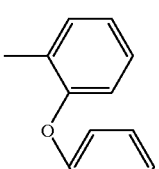 | m.p.: 104° C. |
| 7 | 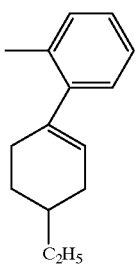 | m.p.: 73° C. |
| 8 | 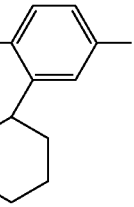 | m.p.: 151° C. |

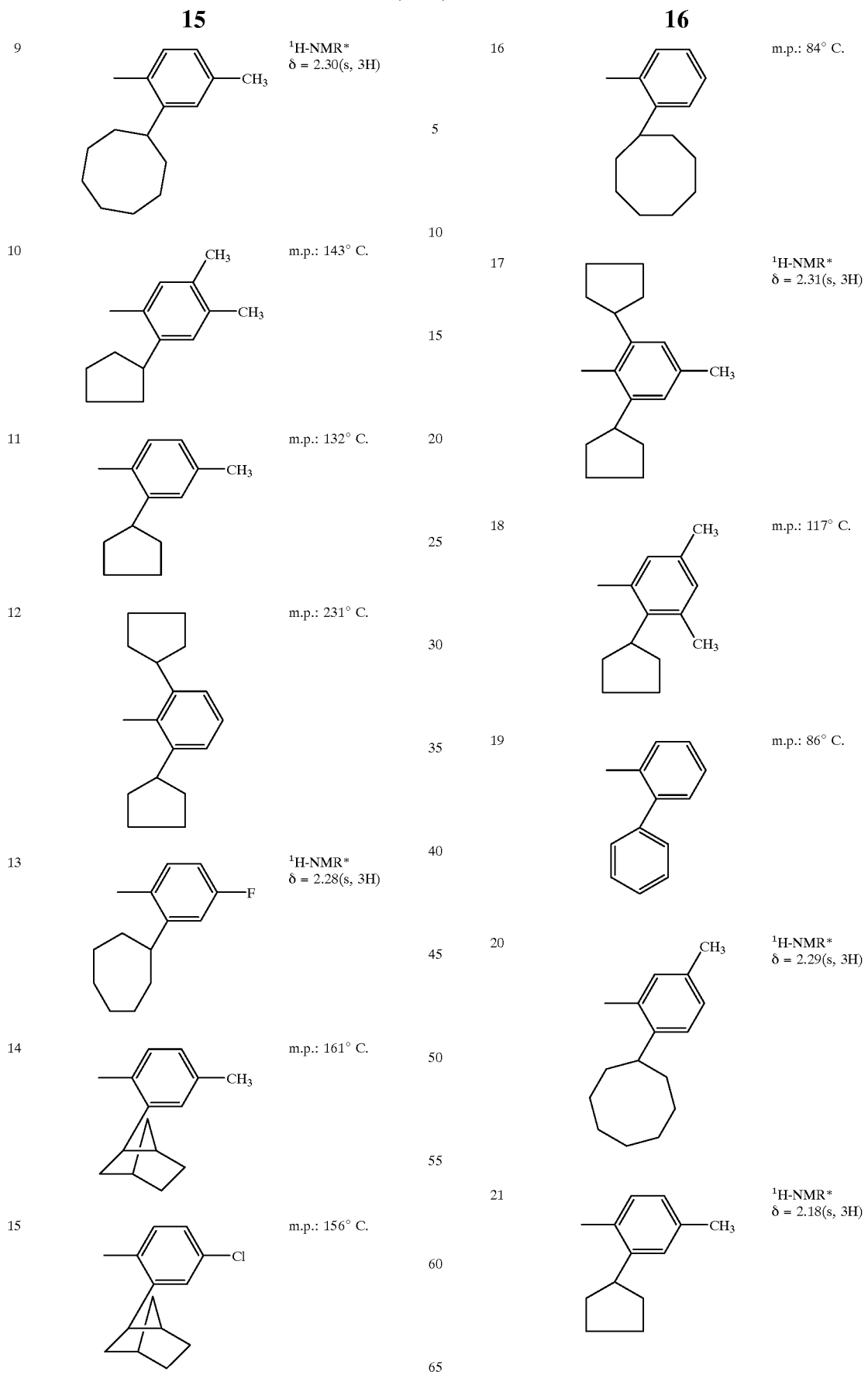

| | | | | | | |
|---|---|---|---|---|---|---|
| 22 | (structure) | m.p.: 221° C. | | 28 | (structure) | m.p.: 108° C. |
| 23 | (structure) | ¹H-NMR* δ = 2.28(s, 3H) | | 29 | (structure) | m.p.: 90° C. |
| 24 | (structure) | m.p.: 116° C. | | 30 | (structure) | ¹H-NMR* δ = 2.16(s, 3H) |
| 25 | (structure) | m.p.: 123° C. | | 31 | (structure) | m.p.: 113° C. |
| 26 | (structure) | m.p.: 170° C. | | 32 | (structure) | ¹H-NMR* δ = 2.16(s, 3H) |
| 27 | (structure) | m.p.: 121° C. | | 33 | (structure) | m.p.: 107° C. |
| | | | | 34 | (structure) (cis/trans) | ¹H-NMR*) δ = 2.23(s, 3H) |
| | | | | 35 | (structure) | m.p.: 118° C. |
| | | | | 36 | (structure) (trans) | m.p.: 165° C. |

| | | |
|---|---|---|
| 37 | 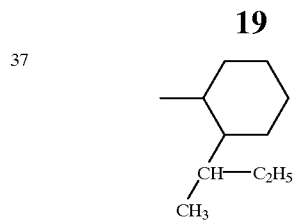 | ¹H-NMR*<br>δ = 2.22(s, 3H) |
| 38 | 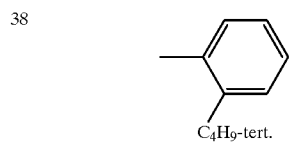 | m.p.: 145° C. |
| 39 | 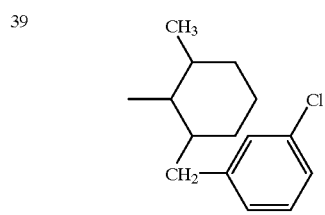 | ¹H-NMR*<br>δ = 2.24(s, 3H) |
| 40 | 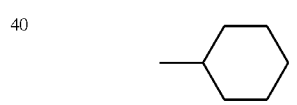 | m.p.: 83° C. |
| 41 | 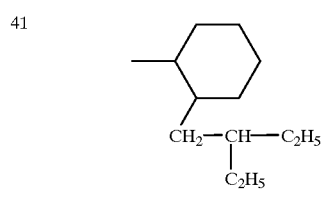 | ¹H-NMR*<br>δ = 2.23(s, 3H) |
| 42 | 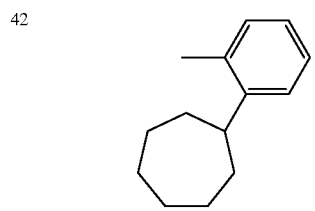 | m.p.: 107–109° C. |

*The ¹H-NMR spectra were recorded in deuterochloroform (CDCl₃) using tetramethylsilane (TMS) as internal standard. Stated is the chemical shift as δ value in ppm.

*) The ¹H-NMR spectra were recorded in deuterochloroform (CDCl₃) using tetramethylsilane (TMS) as internal standard. Stated is the chemical shift as δ value in ppm.

USE EXAMPLES

In the following examples, the compounds listed below were employed as comparative substances:

(A):

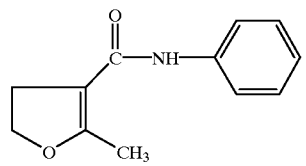

2-methyl-4,5-dihydrofuiran-3-carboxanilide (Known from DE-A 1 914 954)

(B):

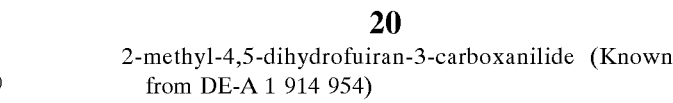

2-methyl-4,5-dihydrofuran-3-N-(1,1,3-trimethylindan-4-yl)-carboxamide (Known from J. Pesticide Sci. 18 (1993), 245–251)

Example A

Botrytis Test (bean)/Protective

Solvent 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, 2 small agar pieces overgrown with Botrytis cinerea are placed onto each leaf. The inoculated plants are placed in a dark humid chamber at 20° C.

3 days after the inoculation, the size of the infected areas on the leaves is determined and expressed in %. 0% means an efficacy which corresponds to that of the control, while an efficacy of 100% means that no infection is observed.

Active compounds, active compound concentrations and test results are shown in the Table below.

TABLE A

Botrytis test (bean)/protective

| Active compound | Efficacy in % at an active compound concentration in the spray liquor of 100 ppm |
|---|---|
| Known | |
| 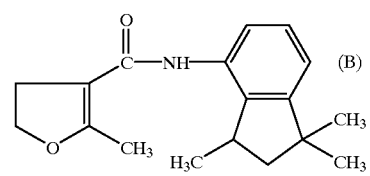 (B) | 57 |
| 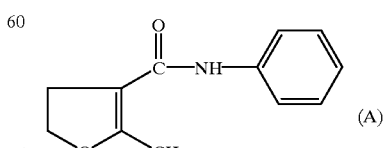 (A) | 33 |

TABLE A-continued

Botrytis test (bean)/protective

| Active compound | Efficacy in % at an active compound concentration in the spray liquor of 100 ppm |
|---|---|
| According to the invention: | |
| 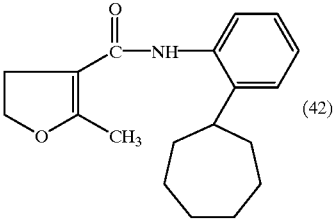 (42) | 94 |
| 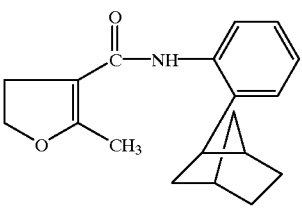 (4) | 92 |

Example B

Erysiphe Test (wheat)/Protective

Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis*f.sp. tritici.

The plants are placed in a greenhouse at a temperature of approximately 20° C. and a realtive atmospheric humidity of approximately 80% to promote the development of mildew pustules.

Evaluation is carried out 7 days after the inoculation. 0% means an efficacy which corresponds to that of the control, while an efficacy of 100% means than no infection is observed.

Active compounds, active compound concentrations and test results are shown in the Table below.

TABLE B

Erysiphe test (wheat)/protective

| Active compound | Efficacy in % at an application rate of active compound of 250 g/ha |
|---|---|
| Known | |
| 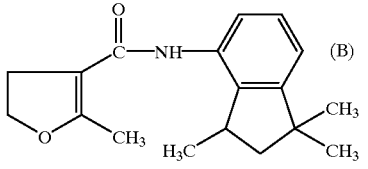 (B) | 27 |
| According to the invention | |
| 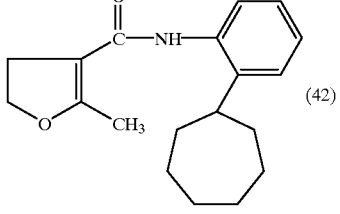 (42) | 73 |

Example C

Sphaerotheca Test (cucumber)/Protective

Solvent: 47 parts by weight of acetone
Emulgator: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with conidia of the fungus *Sphaerotheca fuliginea*.

The plants are subsequently placed in a greenhouse at 23 to 24° C. and at a relative atmospheric humidity of approximately 75%.

Evaluation is carried out 10 days after the inoculation. 0% means an efficacy which corresponds to that of the control, while an efficacy of 100% means that no infection is observed.

Active compounds, active compound concentrations and test results are shown in the Table below.

TABLE C

Sphaerotheca test (cucumber)/protective

| Active compound | Efficacy in % at an active compound concentration in the spray liquor of 100 ppm |
|---|---|
| Known (B) | 25 |
| According to the invention (42) | 77 |
| (16) | 62 |
| (3) | 75 |
| (4) | 70 |
| (8) | 50 |

Example D
Venturia Test (apple)/Protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated with an aqueous conidia suspension of the causative organism of apple scab *Venturia inaequalis* and then remain in an incubation cabin at 20° C. and 100% relative atmospheric humidity for 1 day.

The plants are then placed in a greenhouse at 20° C. and a relative atmospheric humidity of approximately 70%.

Evaluation is carried out 12 days after the inoculation. 0% means an efficacy which corresponds to that of the untreated control, while an efficacy of 100% means that no infection is observed.

Active compounds, active compound concentrations and test results are shown in the Table below.

TABLE D

Venturia test (apple)/protective

| Active compound | Efficacy in % at an active compound concentration in the spray liquor of 100 ppm |
|---|---|
| Known (A) | 71 |
| According to the invention (4) | 86 |
| (42) | 97 |

Example E
Material Protection Test
Inhibition of the growth of wood-destroying Basidiomycetes
Solvent: Dimethyl sulphoxide To produce a suitable preparation of active compound, 0.2 parts by weight of active compound are admixed to 99.8 parts by weight of the abovementioned solvent.

An agar, prepared by using malt extract peptone, is mixed in a liquid state with the preparation of active compound at the application rate desired in each case. After solidification, the resulting nutrient medium is incubated at 27° C. with mycel pieces punched out of colonies of Basidiomycetes.

Evaluation is carried out after 3- or 7-day storage at 27° C. by measuring the growth of the mycelium and scoring the resulting inhibition in per cent in comparison to the untreated control. 0% means an inhibition of growth which corresponds to that of the untreated control, while an inhibition of growth of 100% means that no growth of mycelium is observed.

Active compounds, active compound concentrations and test results are shown in the Table below.

TABLE E

Inhibition of the growth of wood-destroying Basidiomycetes

| Fungal species | Inhibition in per cent of the radial growth of giant colonies at 6 ppm of active compound according to Example | |
|---|---|---|
| | (28) | (42) |
| Gloeophyllum trabeum | 50 | 60 |
| Coniophora puteana | 50 | 60 |
| Poria placenta | 30 | 50 |
| Lentinus tigrinus | 70 | 80 |
| Coriolus versicolor | 70 | 100 |
| Stereum sanguinolentum | 70 | 80 |

What is claimed is:

1. Dihydrofuran-carboxamides of the formula

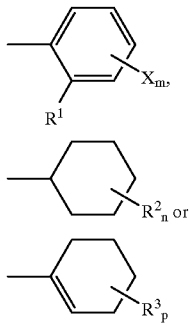

(I)

in which

R represents groupings of the formulae

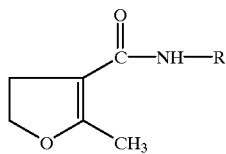

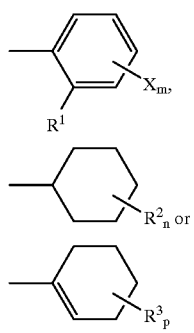

in which
R$^1$ represents optionally substituted cycloalkyl, optionally substituted bicycloalkyl, optionally substituted cycloalkenyl, optionally substituted cycloalkylalkyl, optionally substituted aryl, optionally substituted aroxy, optionally substituted aralkyl or represents alkyl, X represents alkyl having 1 to 6 carbon atoms, halogen, cycloalkyl having 3 to 8 carbon atoms, alkoxy having 1 to 6 carbon atoms, halogenoalkyl having 1 to 4 carbon atoms and 1 to 5 halogen atoms or halogenoalkoxy having 1 to 4 carbon atoms and 1 to 5 halogen atoms, m represents integers from 0 to 3, R$^2$ represents alkyl, cycloalkyl, optionally substituted aryl or optionally substituted aralkyl, n represents integers from 0 to 3, R$^3$ represents alkyl, cycloalkyl, optionally substituted aryl or optionally substituted aralkyl and p represents integers from 0 to 3.

2. Dihydrofuran-carboxamides of the formula (I) according to claim 1, in which

R represents the groupings of the formulae in which
R$^1$ represents cycloalkyl having 3 to 8 carbon atoms which is optionally mono- to trisubstituted by identical or different alkyl groups having 1 to 4 carbon atoms, represents bicycloalkyl having 7 to 12 carbon atoms which is optionally mono- to trisubstituted by identical or different alkyl groups having 1 to 4 carbon atoms, represents cycloalkenyl having 5 to 8 carbon atoms which is optionally mono- to trisubstituted by identical or different alkyl groups having 1 to 4 carbon atoms or represents cycloalkylalkyl having 3 to 8 carbon atoms in the cycloalkyl moiety and 1 to 4 carbon atoms in the alkyl moiety which is optionally mono- to trisubstituted by identical or different alkyl groups having 1 to 4 carbon atoms, or represents phenyl which may be mono- to trisubstituted by identical or different substituents selected from the group consisting of halogen and alkyl having 1 to 4 carbon atoms, or represents phenoxy which may be mono- to trisubstituted by identical or different substituents selected from the group consisting of halogen and alkyl having 1 to 4 carbon atoms, or represents phenylalkyl having 1 to 4 carbon atoms in the alkyl moiety which may be mono- to trisubstituted in the phenyl moiety by identical or different substituents selected from the group consisting of halogen and alkyl having 1 to 4 carbon atoms, or represents straight-chain or branched alkyl having 1 to 12 carbon atoms, X represents straight-chain or branched alkyl having 1 to 4 carbon atoms, fluorine, chlorine, bromine, cycloalkyl having 3 to 8 carbon atoms, straight-chain or branched alkoxy having 1 to 4 carbon atoms, halogenoalkyl having 1 or 2 carbon atoms and 1 to 5 fluorine, chlorine and/or bromine atoms or represents halogenoalkoxy having 1 or 2 carbon atoms and 1 to 5 fluorine, chlorine and/or bromine atoms, m represents the numbers 0, 1 or 2, $R^2$ represents straight-chain or branched alkyl having 1 to 12 carbon atoms, cycloalkyl having 3 to 8 carbon atoms, phenyl which is optionally mono- to trisubstituted by identical or different substituents selected from the group consisting of halogen and alkyl having 1 to 4 carbon atoms or represents phenylalkyl having 1 to 4 carbon atoms in the alkyl moiety which is optionally mono- to trisubstituted by identical or different substituents selected from the group consisting of halogen and alkyl having 1 to 4 carbon atoms, n represents the numbers 0, 1, 2 or 3, $R^3$ represents straight-chain or branched alkyl having 1 to 12 carbon atoms, cycloalkyl having 3 to 8 carbon atoms, phenyl which is optionally mono- to trisubstituted by identical or different substituents selected from the group consisting of halogen and alkyl having 1 to 4 carbon atoms or represents phenylalkyl having 1 to 4 carbon atoms in the alkyl moiety which is optionally mono- to trisubstituted by identical or different substituents selected from the group consisting of halogen and alkyl having 1 to 4 carbon atoms and p represents the numbers 0, 1, 2 or 3.

3. Process for preparing dihydrofuran-carboxamides of the formula (I) according to claim 1, characterized in that 2-methyl-4,5-dihydrofuran-3-carbonyl halides of the formula

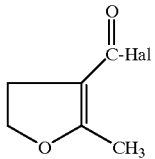
(II)

in which

Hal represents chlorine or bromine, are reacted with araines of the formula

 (III)

in which

R is as defined above, if appropriate in the presence of an acid binder and if appropriate in the presence of a diluent.

4. A microbicidal composition, comprising at least one dihydrofuran-carboxamide of the formula (I) according to claim 1 and one or more extenders and/or surfactants.

5. A method for controlling undesirable microorganisms in crop protection and in the protection of materials, comprising the step of applying a dihydrofuran-carboxamide of the formula (I) according to claim 1 to the microorganisms and/or their habitat.

* * * * *